United States Patent [19]
Habraken

[11] Patent Number: 5,928,149
[45] Date of Patent: *Jul. 27, 1999

[54] ELECTROMAGNETIC OBJECT DETECTOR WITH TEST ELECTRODE FOR A MEDICAL DIAGNOSTIC APPARATUS

[75] Inventor: Wilhelmus J. P. Habraken, Eindhoven, Netherlands

[73] Assignee: U.S. Philips Corporation, New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/843,819

[22] Filed: Apr. 21, 1997

[51] Int. Cl.$^6$ .................................................. A61B 6/00
[52] U.S. Cl. ..................... 600/425; 600/300; 600/407; 128/897; 378/204; 378/207; 340/686
[58] Field of Search ...................................... 600/300, 372, 600/407, 425; 128/897; 378/204, 207; 73/1.79; 340/870.01, 870.04, 870.16, 500, 501, 679, 686; 324/71.1

[56] References Cited

U.S. PATENT DOCUMENTS

| | | | |
|---|---|---|---|
| 5,107,839 | 4/1992 | Houdek et al. | 600/411 |
| 5,414,749 | 5/1995 | Van Alst | 378/172 |
| 5,560,357 | 10/1996 | Faupel et al. | 600/345 |
| 5,570,770 | 11/1996 | Baaten et al. | 192/147 |

FOREIGN PATENT DOCUMENTS

4126168 A1  2/1992  Germany .

*Primary Examiner*—Ruth S. Smith
*Attorney, Agent, or Firm*—Dwight H. Renfrew, Jr.

[57] ABSTRACT

An apparatus for medical diagnosis and/or therapy includes an electromagnetic obstacle sensor in order to prevent collisions with, for example a patient to be examined. The sensor is constructed so as to include a radiation transmitter and a radiation receiver in the form of capacitive electrodes 16 and 18, respectively, whereto electronic circuits 26 and 28 for signal processing are connected. In order to enable the electrodes 16 and 18 and the electronic circuits 26 and 28 to be checked for correct operation, a test electrode 14 is connected between the transmitter electrode 16 and the detection electrode 18, which test electrode can be connected, if desired, to a point 32 of fixed voltage via a controllable switch 34. The presence of an obstacle is thus simulated. The output signal of the electronic circuits 26 and 28 can be checked to determine whether this output signal corresponds to the situation in which an obstacle is present.

15 Claims, 2 Drawing Sheets

ELECTROMAGNETIC OBJECT DETECTOR WITH TEST ELECTRODE FOR A MEDICAL DIAGNOSTIC APPARATUS

BACKGROUND OF THE INVENTION

1. Field of the Invention

The invention relates to an apparatus for medical diagnosis and/or therapy; including a detection device for electromagnetic detection of the presence of an object in the vicinity of a movable part of the apparatus, which detection device includes a transmitter electrode which is connected to the movable part in order to produce an electromagnetic field in the vicinity of the transmitter electrode, a detection electrode which is connected to the movable part and arranged in the vicinity of the transmitter electrode in order to detect an electromagnetic field in the vicinity of the detection electrode, and a receiver which is arranged to receive on an input an input signal which corresponds to the electromagnetic field in the vicinity of the detection electrode, and to produce an output signal which corresponds to the input signal.

2. Description of the Related Art

An apparatus of this kind is known from German published Patent Application DE 41 26 168.

An apparatus for medical diagnosis and/or therapy may include a radiation transmitter and a radiation receiver. An example in this respect is a medical X-ray apparatus which includes an X-ray source and an X-ray detector which is usually referred to as an image intensifier. These two elements are arranged at some distance from one another, the patient to be examined or treated being positioned between the X-ray source and the image intensifier. The X-ray source and the image intensifier are positioned relative to the body of the patient in such a manner that an image can be formed of the desired slice of the body (the "object"). The orientation and position of such apparatus can often be adjusted by means of a motor drive. Generally speaking, in the context of the present invention an object is to be understood to mean the body of a patient to be examined, or an object to be examined otherwise, the body or a part of the body of a person attending the apparatus, parts of the apparatus itself (for example, the patient table) or of neighboring apparatus, or other obstacles which could invade the path of movement of the parts of the apparatus.

Many of such apparatus include a so-called C-arm, i.e. a circular carrier which is rotatable in its own plane (i.e. about an axis extending perpendicularly to the plane in which the C-arm is situated) by way of a guide (trackway) and whose own plane is rotatable about an axis situated in that plane. Moreover, often a number of other possibilities for displacement are provided.

During use of the apparatus it is important that a movable part, for example the image intensifier, closely approaches the object to be examined in order to achieve the desired clarity of the image. The image intensifier has a comparatively large front face for receiving the X-rays and each point on this front face or on its circumference can come into contact with the object to be examined. Such a collision can occur in any direction of movement of the image intensifier. This is undesirable and, therefore, such an apparatus includes a detection device for detecting the presence of an object in the vicinity of the movable part of the apparatus. It is important to provide such a detection device notably in the case of motor-driven apparatus. When an object is detected within a given small distance from the movable part of the apparatus, the movement of (that part of) the apparatus can be stopped so as to avoid a collision.

The cited Patent Application DE 41 26 168 discloses a medical X-ray apparatus which includes an electromagnetic collision sensor enabling detection of the presence of an object within a given, small distance from the movable part of the apparatus. This apparatus includes a signal source for producing an electric signal in the form of a fixed voltage. This voltage is applied to a transmitter electrode in the form of a metal foil. In the vicinity of the metal foil, but electrically insulated therefrom, there is provided a further metal foil which acts as a detection electrode. Between these two metal foils a signal can be measured which corresponds to the electromagnetic field strength in the vicinity of the collision sensor. This signal is further processed by means of a receiver which consists of a number of amplifiers and produces an output signal corresponding to the field strength.

It is desirable that during use of such an apparatus it can be checked that the electrodes and the electronic circuits for signal processing operate correctly. Therefore, in the known collision sensor the voltage from each of the electrodes is applied to a comparator associated with the relevant voltage, the voltage being compared therein with a slightly lower reference voltage. If the voltage from the relevant electrode is absent, the comparator outputs an output signal whose logic value opposes the value of the output signal in the situation in which the voltage from the relevant electrode is present. The output voltages of the comparators are applied to a logic circuit in order to establish the existence of a fault. This method of checking the correct operation of the electrodes and the electronic circuits has the drawback that it requires additional electronic circuits which themselves may also be subject to faults. Consequently, on the one hand the failure of an electrode may thus remain undetected whereas on the other hand a signal representing a fault can be produced even in the case of correct operation of the electrodes. The reliability of the detection device of the apparatus for medical diagnosis and/or therapy is thus adversely affected.

It is an object of the invention to provide an apparatus of the kind set forth in which incorrect operation of the electrodes and/or the electronic circuits coupled thereto can be more reliably detected.

To this end, the apparatus according to the invention is characterized in that the detection device includes a test electrode which is connected to the movable part and is arranged in the vicinity of the transmitter electrode and the detection electrode, a controllable switch which is connected between the test electrode and a point carrying a fixed voltage, and a control unit for controlling the state of conductivity of the switch.

In normal operating conditions the controllable switch is in the non-conductive state. When information is desired concerning the operation of the electrodes and the associated electronic circuits, the switch is set to the conductive state by means of the control unit for controlling the state of conductivity of the switch. The test electrode is thus connected to the point of fixed voltage so that the electromagnetic field in the vicinity of the electrodes exhibits the same change as if an obstacle were present in the vicinity of the movable part of the apparatus. The presence of an obstacle is thus simulated by driving the switch to the conductive state. By observation of the output signal produced by the receiver for receiving a signal corresponding to the electromagnetic field in the vicinity of the detection electrode it can be checked whether the output signal corresponds to the situation in which an obstacle is present. If this is not the case, it is practically excluded that the cause lies outside the electrodes or the electronics.

Further embodiments of the invention are disclosed in the dependent claims.

These and other aspects of the invention will be apparent from and elucidated with reference to the embodiments described hereinafter.

DETAILED DESCRIPTION OF THE PREFERRED EMBODIMENTS

Figure 1:
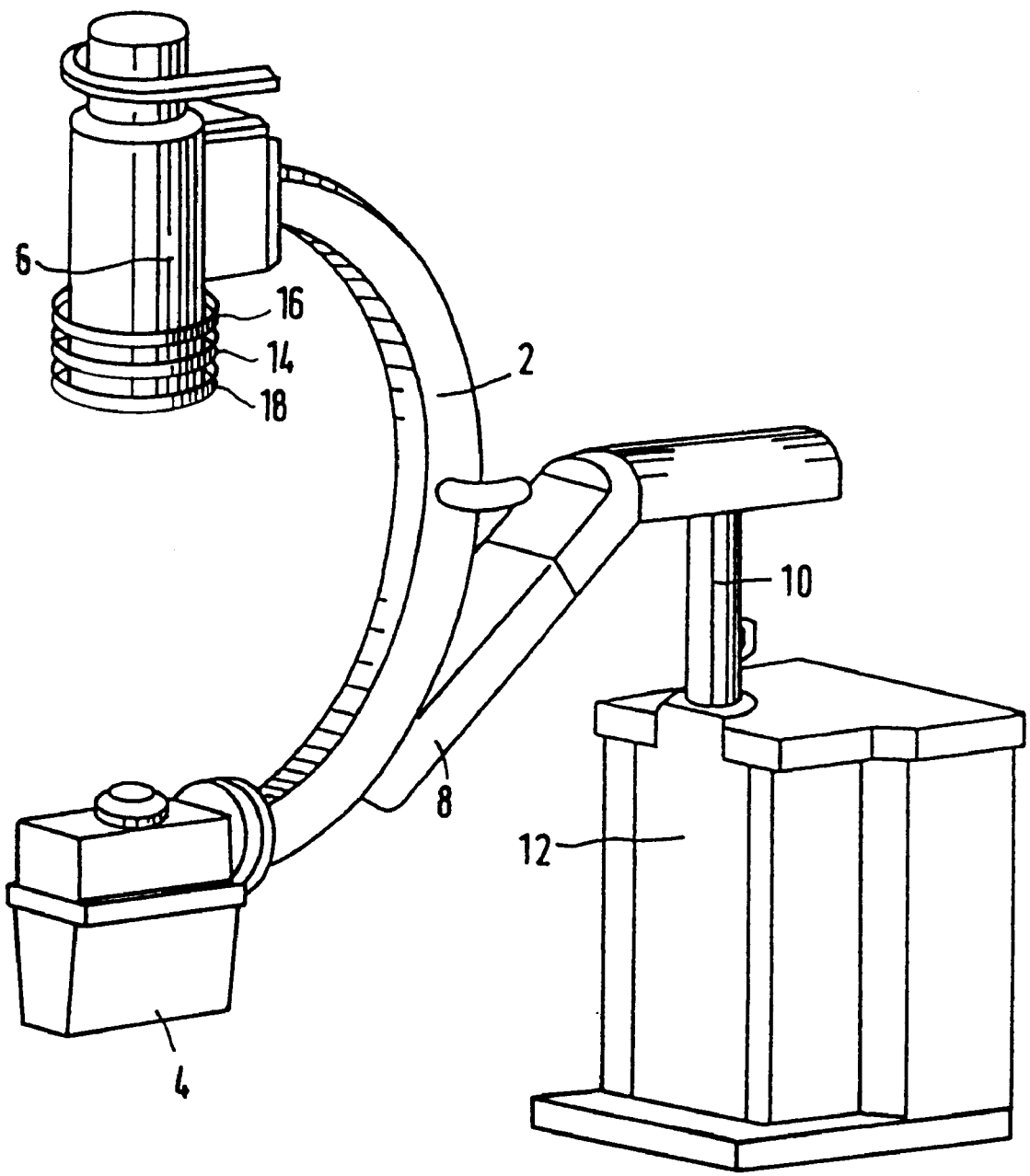
FIG. 1 is a general view of a medical X-ray apparatus in which electromagnetic detection of the presence of an obstacle can be used.

FIG. 1 is a general view of a medical diagnostic and/or therapy apparatus in the form of an X-ray apparatus. The X-ray apparatus is constructed so as to include a carrier 2 on which an X-ray source 4 and an X-ray image intensifier 6 are mounted. The carrier is shaped as an arc of circle so that it can be rotated about an axis extending perpendicularly to the plane of the arc of circle by means of a guide (trackway) 8. This type of carrier is known as a C-arm; generally speaking, they are also rotatable about an axis extending in the plane of the arc of circle. The rotation mechanism for the latter movement is not shown in the Figure. The assembly formed by the carrier 2 and the guide 8 is also rotatable about a shaft 10. This shaft is mounted on a stand 12 which may be constructed so as to be mobile, if desired. The X-ray source 4 and the X-ray detector 6 preferably are also displaceable relative to the carrier 2. For easy displacement of these components they are constructed so as to include a motor drive which is not shown in the figure. The object to be examined, in this case being the body of the patient to be examined or treated, is arranged on a table (not shown) which is positioned between the image intensifier 6 and the X-ray source 4. As a result of the described possibilities of movement of the C-arm 2, the image intensifier 6 and the X-ray source 4, these components can be positioned in all desirable directions relative to the patient and images can be formed of all desired slices.

Because of their mobility, the movable parts, such as the image intensifier 6 and the X-ray source 4, can readily come into contact with the body of the patient to be examined or with other obstacles. This is undesirable and, therefore, the image intensifier of the present embodiment is provided with a detection device for detecting the presence of an object in the vicinity of the movable part of the apparatus. The detection device includes a transmitter electrode 16 and a detection electrode 18. The transmitter electrode 16 is shaped as an annular electrode which is arranged around the end of the image intensifier 6 in order to produce an electromagnetic field in the vicinity of this electrode. The detection electrode 18 is shaped as an annular electrode 18 which is arranged around the end of the image intensifier 6 and in the vicinity of the transmitter electrode 16 in order to detect the electromagnetic field produced by the transmitter electrode 16 and distorted by the object to be detected. The annular electrodes 16 and 18 can be subdivided into ring sectors in order to achieve directional sensitivity, the signal originating from each ring sector of the transmitter electrode being detected separately by means of the associated sector of the detection electrode. Between the transmitter electrode 16 and the detection electrode 18 there is arranged a test electrode 14 whose operation will be described in detail hereinafter with reference to FIG. 2. The transmitter electrode 16, the test electrode 14 and the detection electrode 18 are constructed so as to be strip-shaped in the present embodiment and are provided around the outer surface of the cylindrically shaped image intensifier 6. Around this cylindrical outer surface the strip-shaped electrodes are arranged parallel to one another and in the same cylinder plane.

Figure 2:
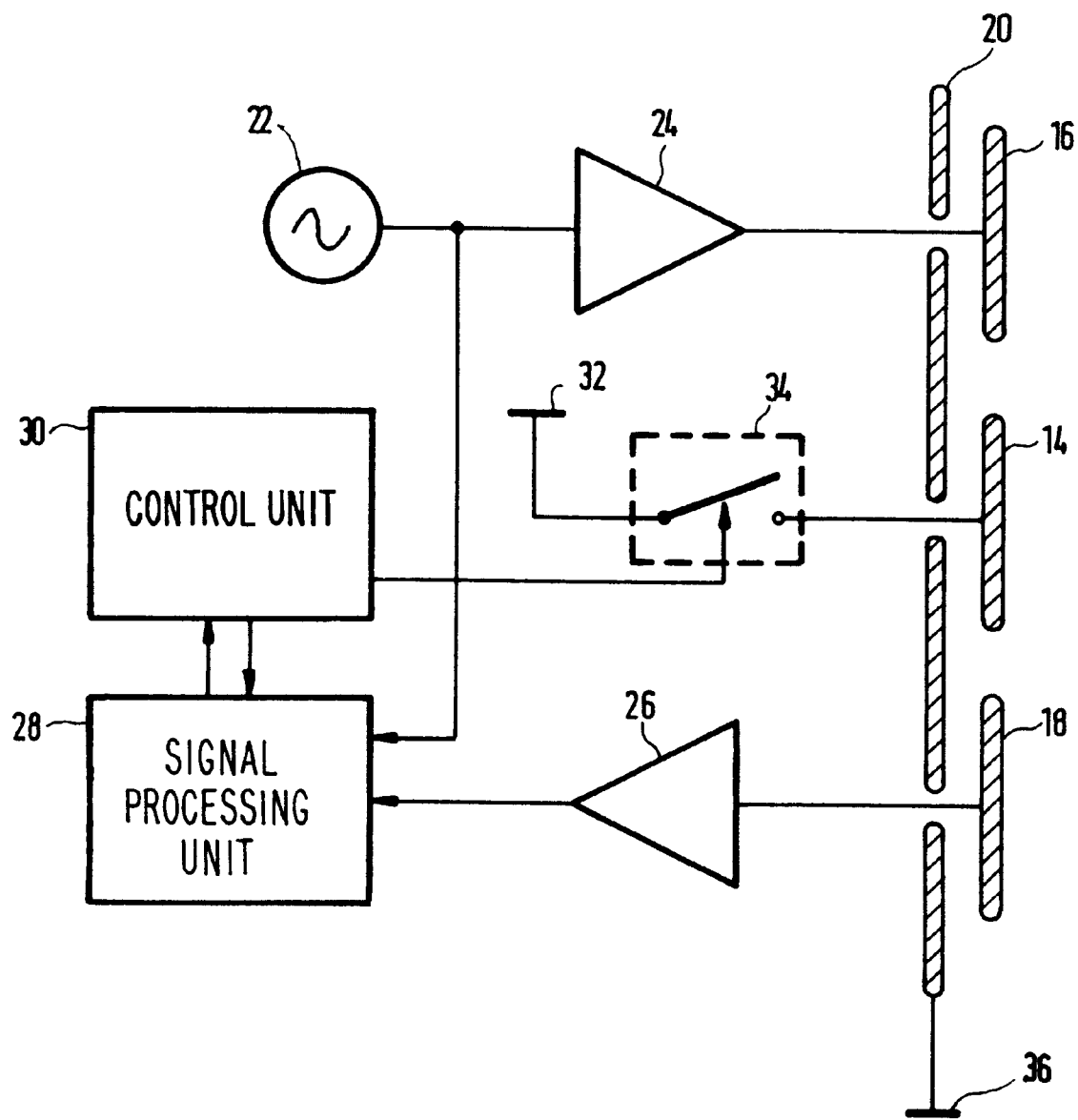
FIG. 2 shows diagrammatically a detection device according to the invention.

FIG. 2 is a diagrammatic view of the detection device according to the invention. A signal source 22 produces a sinusoidal electric signal which has an amplitude of the order of magnitude of 5 V and a frequency of the order of magnitude of 100 kHz. The signal source 22 is connected, via a buffer amplifier 24, to the transmitter electrode 16 which produces an electromagnetic field corresponding to the electric signal in the vicinity of the transmitter electrode 16. The electrode 16 is situated outside the housing 20 of the image intensifier 6. The housing 20 is connected to a point 36 carrying a fixed voltage which is referred to as system ground.

The electromagnetic field produced by the transmitter electrode 16 produces an electric signal in the detection electrode 18, which signal is applied to the input of an amplifier 26. The electrode 18 is also situated outside the housing 20 of the image intensifier 6. Via signal processing means which are not of relevance to the invention and hence are not shown in the Figure (for example, a bandpass filter and a synchronous detector), the output signal of the amplifier 26 is applied to a signal processing unit 28. Said signal processing means may form part of the unit 28. In conjunction with the signal processing unit 28 the amplifier 26 forms a receiver for receiving an input signal corresponding to the electromagnetic field in the vicinity of the detection electrode (18).

The signal produced by the signal source 22 is applied to the electrode 16 via the buffer amplifier 24. It is assumed that initially no object is present in the vicinity of this electrode. A capacitive coupling exists between the electrodes 16 and 18, so that the electric field produced by the electrode 16 induces an electric signal in the electrode 18. This signal is amplified by the amplifier 26 so as to form a signal whose value is a measure of the amplitude of the input signal. The output signal of the signal source 22 is also applied to the signal processing unit 28 in which a DC signal is produced, for example by means of a synchronous detector. When a grounded object (for example, a patient to be examined by means of the X-ray apparatus) approaches the electrodes 16 and 18, the voltage on the input increases due to the capacitive coupling between the electrodes, and hence said DC signal also increases. This DC signal indicates whether an obstacle is situated so close to the image intensifier that a control operation is required, this signal thus being used to control the movement of the movable parts of the apparatus. This method of control, however, does not form part of the invention and, therefore, will not be elaborated herein.

During use of the X-ray apparatus it is desirable that the signal source 22, the electrodes 16 and 18 and the electronic circuits 26 and 28 for signal reception and processing can be checked for correct operation. To this end there are provided a control unit 30 which is connected to the signal processing unit 28, and a controllable switch 34 which is connected between the test electrode 14 and a point 32 carrying a fixed voltage, the control unit 30 being arranged to control the state of conductivity of the switch 34. Before or during operation of the X-ray apparatus the switch 34 can be set to its conductive state as desired by the operating staff or automatically under the control of the control unit 30. The test electrode 14 is then connected to the point 32 carrying a fixed voltage so that the electromagnetic field in the vicinity of the electrodes 16 and 18 changes in the same way as if an obstacle were present in the vicinity of the movable part 6 of the X-ray apparatus. Thus, the presence of an obstacle is simulated by controlling the switch 34 to the conductive state. By observing said DC signal in the signal processing unit 28, it can be detected whether this output signal corresponds to the situation in which an obstacle is present. If this is not the case, it may be concluded that there is a fault whose cause lies practically certainly in the signal source 22, the electrodes 16 or 18 or the electronic circuits 26 and 28 for signal reception and processing.

I claim:

1. A detection device for detecting the presence of an object in the vicinity of a movable part of an apparatus for medical diagnosis or therapy, said device comprising:

a transmitter electrode for arrangement on the moveable part for generating an electromagnetic field, a detection electrode for arrangement on the moveable part for producing an input signal responsive to an electromagnetic field in a vicinity of said detection electrode, the electromagnetic field in a vicinity of said detection electrode being responsive in turn to both the electromagnetic field generated by said transmitter electrode and also the presence of an object in a vicinity of said transmitter electrode or of said detection electrode, a receiver responsive to the input signal produced by said detection electrode and for producing an output signal corresponding to the input signal, a test electrode for arrangement on the moveable part in a vicinity of said transmitter electrode and of said detection electrode such that the electromagnetic field in a vicinity of said detection electrode is similarly responsive to a fixed voltage applied to said test electrode as to the presence of an object in a vicinity of said transmitter electrode or of said detection electrode, and means for providing a fixed voltage to said test electrode.

2. The device claimed in claim 1, wherein the transmitter electrode, the test electrode, and the detection electrode are constructed so as to be strip-shaped and are arranged in parallel planes.

3. The device claimed in claim 2, wherein the test electrode is arranged between the transmitter electrode and the detection electrode.

4. The device of claim 2 wherein said transmitter electrode and said detection electrode are divided into sectors, whereby the detection device achieves directional sensitivity.

5. The device claimed in claim 1, wherein the test electrode is arranged between the transmitter electrode and the detection electrode.

6. The device of claim 1 wherein said transmitter electrode and said detection electrode are divided into sectors, whereby the detection device achieves directional sensitivity.

7. The device of claim 1 wherein said means for providing a fixed voltage comprises a switch having a controllable state of conductivity.

8. The device of claim 7 wherein said means for providing a fixed voltage further comprises a control unit, and wherein the state of conductivity of said switch is responsive to the control unit.

9. The apparatus of claim 1 wherein said transmitter electrode and said detection electrode comprise a plurality of ring sectors.

10. A medical apparatus comprising:

a radiation transmitter, a radiation receiver, said radiation transmitter and said radiation receiver being positioned so that an image can be formed of an object to be examined, a moveable part for orienting and positioning said radiation transmitter and said radiation receiver with respect to the object, a transmitter electrode arranged on said moveable part for generating an electromagnetic field, a detection electrode arranged on said moveable part for producing an input signal responsive to an electromagnetic field in a vicinity of said detection electrode, the electromagnetic field in a vicinity of said detection electrode being responsive in turn to both the electromagnetic field generated by said transmitter electrode and also to the presence of an object in a vicinity of said transmitter electrode or of said detection electrode, a receiver responsive to the input signal produced by said detection electrode and for producing an output signal corresponding to the input signal, a test electrode arranged on said moveable part in a vicinity of said transmitter electrode and of said detection electrode such that the electromagnetic field in a vicinity of said detection electrode is similarly responsive to a fixed voltage applied to said test electrode as to the presence of an object in a vicinity of said transmitter electrode or of said detection electrode, and means for providing a fixed voltage to said test electrode.

11. The device of claim 10 wherein said means for providing a fixed voltage comprises a switch having a controllable state of conductivity.

12. The device of claim 11 wherein said means for providing a fixed voltage further comprises a control unit, and wherein the state of conductivity of said switch is responsive to the control unit.

13. The apparatus of claim 10 wherein said radiation transmitter is an x-ray source, wherein said radiation receiver is an x-ray receiver, and wherein said moveable part is a carrier on which said x-ray source and said x-ray transmitter are mounted.

14. The apparatus of claim 13 wherein said x-ray receiver is an x-ray image intensifier.

15. The apparatus of claim 10 wherein said transmitter electrode and said detection electrode comprise a plurality of ring sectors.

* * * * *